United States Patent [19]
Rakos et al.

[11] Patent Number: 6,015,432
[45] Date of Patent: Jan. 18, 2000

[54] WIRE REINFORCED VASCULAR PROSTHESIS

[75] Inventors: Ronald Rakos, Monmouth Junction; Signe Mary Lund, Bedminster; Charles V. Tomonto, Neshanic Station, all of N.J.

[73] Assignee: Cordis Corporation, Miami Lakes, Fla.

[21] Appl. No.: 09/030,408

[22] Filed: Feb. 25, 1998

[51] Int. Cl.$^7$ ...................................................... A61F 2/06
[52] U.S. Cl. ................................................................ 623/1
[58] Field of Search ................................ 623/1, 11, 12; 606/195

[56] References Cited

U.S. PATENT DOCUMENTS

| | | | |
|---|---|---|---|
| 5,057,092 | 10/1991 | Webster | 623/1 |
| 5,366,504 | 11/1994 | Andersen et al. | 623/11 |
| 5,476,506 | 12/1995 | Lunn | 623/1 |
| 5,487,858 | 1/1996 | Schmitt | 623/1 |
| 5,489,295 | 2/1996 | Piplani | 623/1 |
| 5,733,327 | 3/1998 | Igaki | 623/1 |

OTHER PUBLICATIONS

Three–Year Experience with the White–Yu Endovascular GAD Graft for Transluminal Repair of Aortic and Ilias Aneurysms, J. Endovasc. Surg., White et al., 1997, pp. 124–136.

A New Nonstented Balloon–Expandable Graft for Straight or Bifurcated Endoluminal Bypass, J. Endovasc Surg., White et al., 1994, pp. 16–24.

Endovascular Grafting for the Treatment of Abdominal Aortic Aneurysms, Endovascular Surgery, Harrison M. Lazarus, MD, vol. 72, No. 4, Aug. 1992, pp. 959–968.

Tantalum–Dacron Coknit Stent for Endovascular Treatment of Aortic Aneurysms: A preliminary Experimental Study, Piquet et al., J. of Vascular Surgery, vol. 19, Apr. 1994, pp. 689–706.

*Primary Examiner*—Michael J. Milano
*Attorney, Agent, or Firm*—Paul A. Coletti

[57] ABSTRACT

What is described herein is a endovascular tube or bifurcated prosthesis used for the repair of aneurysms or other vessel disease. This can be soft or hard occlusive disease. This prosthesis is constructed by fabricating a structure that consists of a textile or other polymeric material and through which is threaded a superelastic metal wire such as a nitinol, a ductile wire or other filament material. The textile can be a polymeric material. The wire provides the self-expandability of the current device. Ideally, the thickness of the device should be minimized, so that it can be delivered to the diseased site using a percutaneous procedure.

16 Claims, 2 Drawing Sheets

WIRE REINFORCED VASCULAR PROSTHESIS

FIELD OF THE INVENTION

In general, this invention relates to prosthetic devices used for the repair of aneurysms or other vessel disease, including soft or hard occlusive diseases. More specifically, this invention is related to prostheses which are constructed by a weaving, braiding or other process using two different types of materials, typically a superelastic metal wire mesh such as nitinol and a polymeric material.

BACKGROUND OF THE INVENTION

Graft materials are known in the art. However, the current graft materials have certain disadvantages. First of all most graft materials are not self-expanding. In addition, the prosthesis will not typically need a radial crimping to give the prosthesis a shape, kink resistance or twist resistance. Current prostheses are not known to provide such a benefit. Naturally, it is desired to have a stronger, easier to construct device as compared to present prosthesis.

Further, it is desirable to have a graft, which does not need a stent placed at one or both ends of the graft, in order to firmly embed the graft into the lumen of the body. Further, naturally, it is desirable to have a device wherein the superelastic material does not protrude from the outside of the graft. In fact, it is most desirable to have a device where the wire is co-extensive with the textile or other material from which the graft is formed.

SUMMARY OF THE INVENTION

These and other objects of the invention are described by the current device. What is described herein is a endovascular tube or bifurcated prosthesis used for the repair of aneurysms or other vessel disease, which can be either soft or hard occlusive disease. This prosthesis is constructed by fabricating generally a tubular structure that consists of a textile or other polymeric material and through which is threaded a superelastic metal wire such as: nitinol; a ductile wire; or other filament material. The textile can be a polymeric material such as polyethyleneteraphthalate PET or a biocompatible polymer. The wire, if it is superelastic provides the self-expandability of the current device.

Ideally, the thickness of the device should be minimized, so that it can be delivered to the diseased site using a percutaneous procedure, typically catherization. When a superelastic material is used in the interweave of the device, the wire is "set" prior to the textile fabrication. In other words, the "set" takes place when the wire is manufactured or annealed, so that the wire is capable of returning to a particularly identified shape. In this fashion, the wire can be placed within the delivery device and then released so that is expands into position.

The wire is straightened and incorporated with the polymeric material as a component structure. The prosthesis is then heat set as necessary and loaded into a delivery system. Upon delivery, the superelastic wire returns or self-expands to its set shape.

In the case of a woven structure, the wire can be either formed from a wrapped yarn (running lengthwise) or a "filling" yarn (running crosswise). If the device contains a wrap yarn, the yarn can be shape set into a "sawtooth" pattern, so that when it is expanded it forms a crimp-like serration on the prosthesis surface. This gives the prosthesis clear longitudinal flexibility for sizing to the vessel diameter at the luminal wall, as well as a certain amount of radial strength from the self-expanding material.

To obtain the desired self-expanding properties any number of superelastic wires can be run parallel to the longitudinal axis of the prosthesis. Or, the wires can be interposed circumferentially about the prosthesis. In either event, upon self-expansion, the prosthesis sets with a desired outer diameter or in a desired diametral or angle, and becomes firmly implanted against the vessel wall. Because the material is rather impermeable to fluid flow, the aneurysmal area is bridged and healing of the aneurysm can begin. Or, if a lesion is bridged, the superelastic aspects of the device cause the material to expand and take the shape of the graft enlarged lumen, so formed by the disclosed bi-directional graft material. Or, a area which has more direct correlation to Young's modulus can be used, so that the prostheses is more balloon expandable.

DETAILED DESCRIPTION OF THE DRAWINGS

The objects of the invention will be better understood from the following figures.

DETAILED DESCRIPTION OF THE INVENTION

Figure 1:
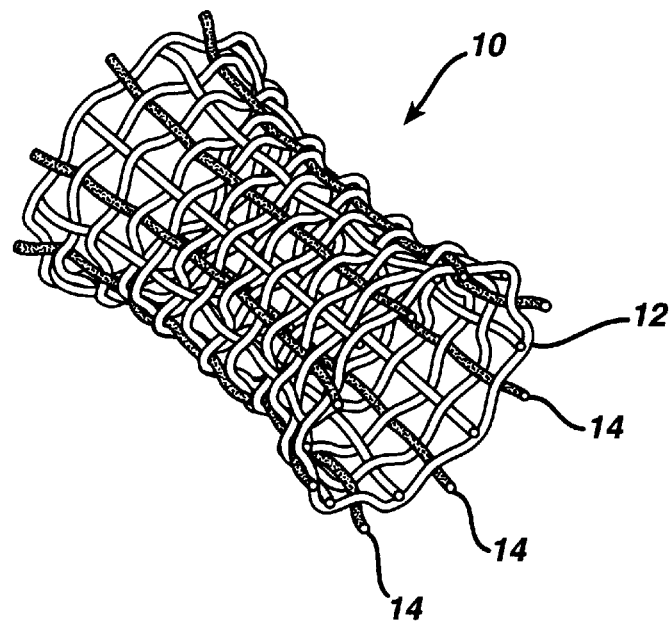
FIG. 1 is a perspective view of the reinforced endovascular prosthesis.
Figure 2:
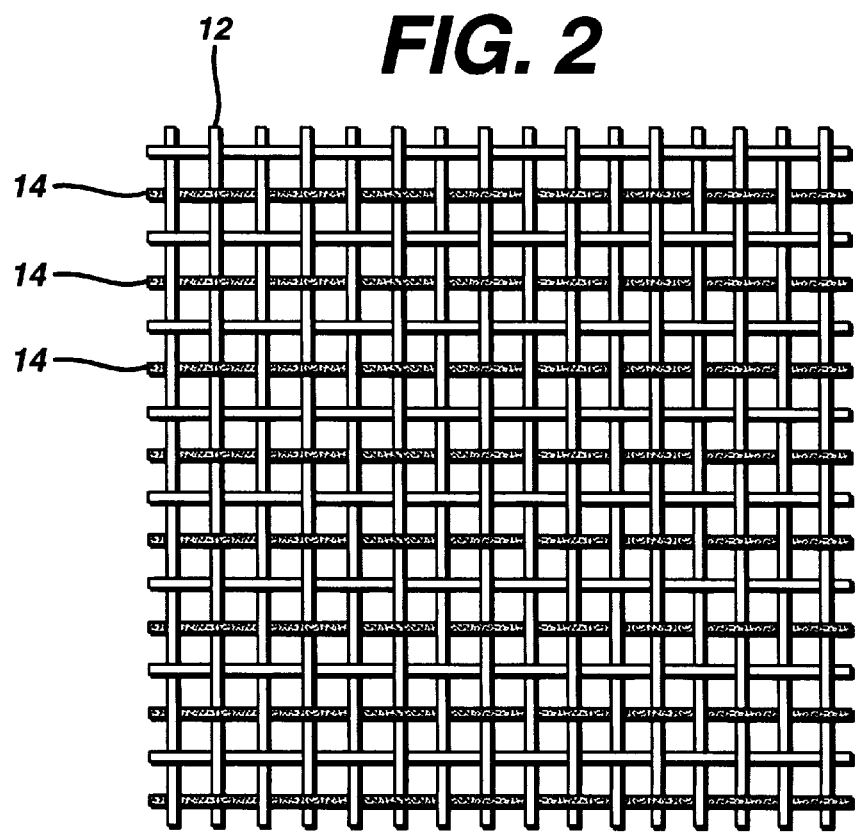
FIG. 2 is the flat braid weave from which the fabrication mechanism from which the device is put into place.
Figure 3:
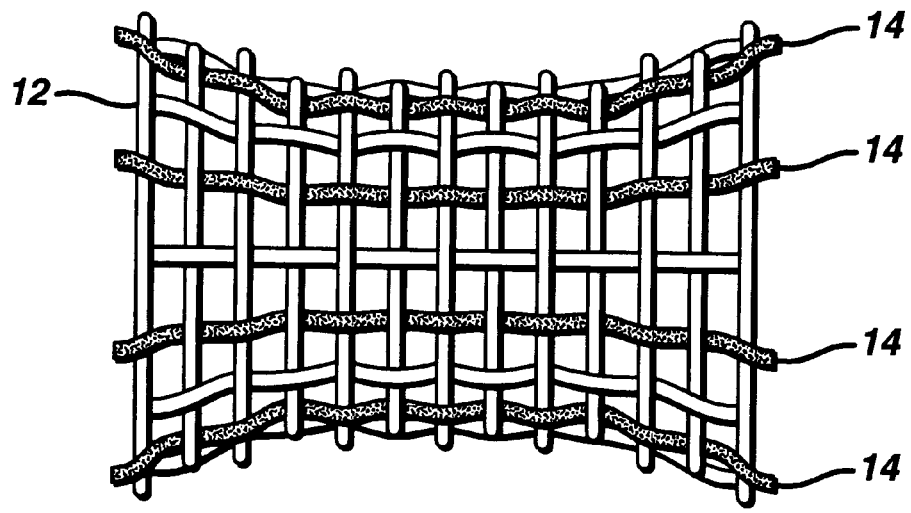
FIG. 3 is a side view of the tubular prosthesis.
Figure 4:
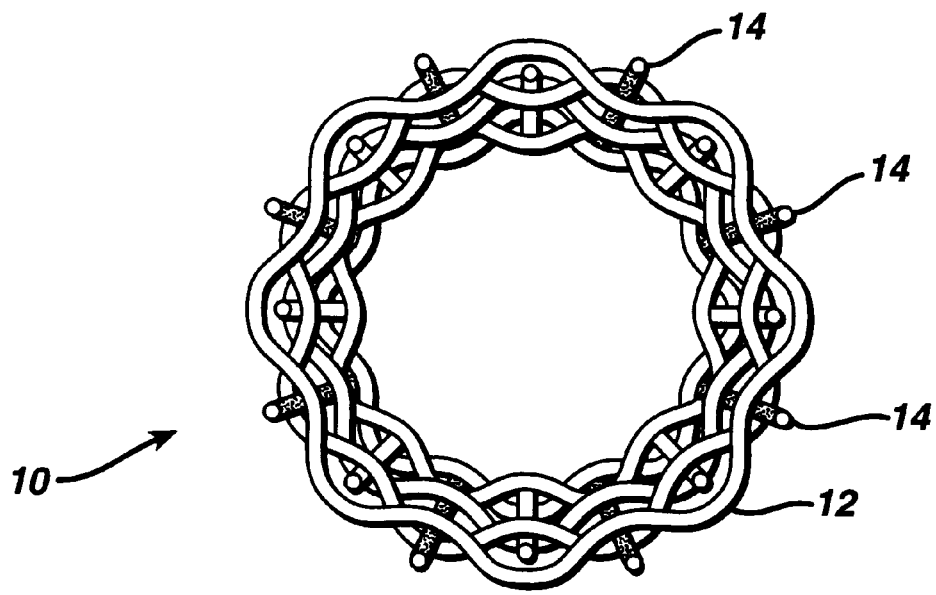
FIG. 4 is an end view of the weave of the tubular prosthesis.

As can be seen from the figures, a device 10 is formed from a graft material 12. The graft material 12 is a woven mesh such as Dacron® or a biocompatible graft 12 on polymer graft. Interposed within interstitial spaces of the device 10 is a series of self-expanding wires 14. These wires 14 are generally placed lengthwise as can be seen in FIGS. 1 and 3. However, as in FIG. 2, the wires 14 are placed circumferentially around the graft 10. In either event, it is the self-expandability of nitinol that proves useful to enhance the particular working qualifications of the Dacron® graft material 12. As seen in FIGS. 3 and 4, in that is the side view and end view figures, it can be shown that the graft 12 is formed so that the wires 14 expand after having been woven through the graft 12. This, of course, causes the device itself to expand upon release within a desired lumen of the body.

Typically, the wire 14 is chosen from a self-expanding material such as nitinol. Of course, wire 14 can be made from some other sort of ductile wire or other filament material. The only necessity is that the structural integrity provided by the wire or other filament be interposed within the graft, as can be seen from the weaves of FIGS. 1–4. If a superelastic material is used, such that the graft can be expanded without need for a balloon, then of course the wire will provide a certain advantage over current self expanding stent-graft combinations, that is, an ability to reduce the overall diametral width of the wire/graft device. This is accomplished due to the combined weave and graft occurring in the same diametral thickness.

So, as can be readily seen, this design is unique in that the superelastic or ductile wire or other filament material is fully incorporated into the textile structure of the polymer base material. Furthermore, it is unique in that the prosthesis itself can be made to be self-expanding.

The prosthesis 10 does not need to be radially crimped, like some precursor devices, due to its integral construction.

The nitinol material (in the self-expanding version); or the steel or other filament material (in the balloon expandable version) forms the prosthesis backbone and provides the prosthesis with structure and integrity as well as providing a strengthening device for the graft to prevent proliferation of occlusive are typically or other aneurysmimal disease. Further, the wires 14 are more radiopaque than the textile structure, and will make the entire prosthesis radiopaque and this more readily visible under X-ray in the body.

Depending on the construction and configuration of the supporting backbone material, stents of either superelastic, ductile or combination of materials can be placed on either end of the prosthesis 10 to anchor the prosthesis 10 to the body wall. However, as can be seen, with the current invention, stents are not per se necessary to provide support to the system.

Naturally, because the superelastic nitinol material is provided within the shape of the current device, it is typically thinner than a layered approach using a stent and a graft combination when the wire 14 is placed on the interior (where it is exposed to the interior side of the graft 12) prosthesis 10 is held by force against the luminal wall.

Finally, if desired, the ductile or superelastic wire 14 with a loosely wrapped textile graft 12 can be made to be extremely porous. Additionally, the device can tightened (as indicated in the Figures) so that the pore sizes (P) are much less than about 30 microns. This enables the device to provide adequate protection for the coronary artery system, which is one intentional area of use.

In use therefore, the device 10 of the present invention is formed by interweaving a nitinol 14, typically a superelastic nitinol, into a Dacron® or Teflon® graft 12. Upon weaving, the device is given a "memory" so that it will take a permanent set at a certain size. Then, the device 10 is compressed into a catheter or other delivery system (not shown) useful for delivering self-expanding stents. When this happens, the device is further compressed and placed in the catheter and furthermore placed in the body. The device is presented to the lesion site in the same way as is done by typical self-expanding stent users. Thereafter, when in place, a sheath (not shown) of the stent delivery system is pulled back, and the device 10 is released. This allows the device 10 to be placed at the lesion site, and with little blood leakage. This provides capable application for either aneurysmal or occlusive disease. Once the prosthesis 10 is in place, the device prevents blood flow and turbulence and pressure on an aneurysm at the situs of graft 10. With respect occlusive disease, the prosthesis 10 can be passed into a lesion of about 1–2.5 mm. By doing so, the occlusive disease (or the aneurysmal area is hopefully well treated.

Minor modifications are certainly possible without departing from the scope of the invention. For instance, the wire materials can be substituted to be either stainless steel, stiffer polymer materials, tantalum or cobalt based superalloys. Whereas the superelastic wires are intended to be self-expanding and supporting, other materials can be interwoven or braided as into the prosthesis 10 to create a self-expanding prosthesis. The wires can be placed in such a manner as to obviate the need for stents on one end of the construction, and more typical grafts on the other end. Naturally, the prosthesis itself can either be straight, tapered or bifurcated. The device can be formed into any shape to conform to various vessel configurations and differing anatomies.

The invention certainly can be used to treat in other conditions such as TIPPS (trans intrahapetic peripheral prosthetic surgeries), diffusive occlusive disease, and soft tissue occlusions where a covered stent would normally be used. The wire can be coated with a textile material such that the prosthesis itself presents uniform biocompatible surface to the body. Or, multiple types of metal wires can be incorporated into the prosthesis to make it more or less radiopaque, as well as to restrict the superelastic material from over-dilating the vessel wall. Depending on the application, the wire or textile can be coated with therapeutic agents such as rapamycin to enhance or retard endothelization of the prosthesis.

Naturally, all these modifications are considered part of the invention. The invention therefore is to be known from the attached claims and their structural and other equivalents.

What is claimed is:

1. A prosthesis comprising a non-metallic woven graft material, said woven graft material having a plurality of openings in its structure; and at least one essentially straight wire emplaced in said plurality of openings in an alternating fashion so as to describe a weave.

2. A prosthesis of claim 1 wherein the wire is a self-expanding alloy.

3. A prosthesis of claim 1 wherein the wire is an alloy which conforms to Young's modulus.

4. A prosthesis of claim 1 wherein the graft is a Dacron® weave.

5. A prosthesis of claim 1 wherein the graft is a Teflon® weave.

6. The prosthesis of claim 1 wherein the prosthesis is self-expanding.

7. The prosthesis of claim 1 wherein the prosthesis is made with said wires placed circumferentially about said graft.

8. The prosthesis of claim 1 wherein the prosthesis is made with said wires placed longitudinally about said graft.

9. A method for placement of a graft, comprising:

providing a prosthesis comprising a non-metallic woven graft material, said woven graft material having a plurality of openings in its structure; and at least one essentially straight wire emplaced in said plurality of openings in an alternating fashion so as to describe a weave.

10. Method of claim 9 wherein the wire is a self-expanding alloy.

11. Method of claim 9 wherein the wire is an alloy which conforms to Young's modulus.

12. Method of claim 9 wherein the graft is a Dacron® weave.

13. Method of claim 9 wherein the graft is a Teflon® weave.

14. Method of claim 9 wherein the prosthesis is self-expanding.

15. Method of claim 9 wherein the prosthesis is made with said wires placed circumferentially about said graft.

16. Method of claim 9 wherein the prosthesis is made with said wires placed longitudinally about said graft.

* * * * *